US006897311B2

(12) United States Patent
Argese et al.

(10) Patent No.: US 6,897,311 B2
(45) Date of Patent: May 24, 2005

(54) PROCESS FOR THE PREPARATION OF DECAHYDRO-2A,4A,6A,8A-TETRAAZACYCLOPENT[FG] ACENAPHTHYLENE AND FUNCTIONALIZED DERIVATIVES

(75) Inventors: Maria Argese, Milan (IT); Marino Brocchetta, Milan (IT); Giuseppe Manfredi, Milan (IT); Fabrizio Rebasti, Milan (IT); Giorgio Ripa, Milan (IT)

(73) Assignee: Bracco International BV, Amsterdam (NL)

( * ) Notice: Subject to any disclaimer, the term of this patent is extended or adjusted under 35 U.S.C. 154(b) by 20 days.

(21) Appl. No.: 10/257,033
(22) PCT Filed: Apr. 10, 2001
(86) PCT No.: PCT/EP01/04092
§ 371 (c)(1), (2), (4) Date: Nov. 25, 2002
(87) PCT Pub. No.: WO01/79207
PCT Pub. Date: Oct. 25, 2001

(65) Prior Publication Data
US 2004/0014974 A1 Jan. 22, 2004

(30) Foreign Application Priority Data
Apr. 14, 2000 (IT) ................................. MI2000A000835

(51) Int. Cl.$^7$ ............................................ C07D 241/36
(52) U.S. Cl. ........................................................... 544/343
(58) Field of Search .......................................... 544/343

(56) References Cited

FOREIGN PATENT DOCUMENTS

WO      96/28432 A      9/1996

OTHER PUBLICATIONS

"Diethyl Oxalate" Material Safety Data Sheet, published by Morflex, Inc. (1999).*
Herve et al; "Condensation of Glyoxal with Triethylenetetraamine; Isomerisation and Cyclisation"; Eur. J. Org. Chem., 2000, pp. 33–35, XP002175525.

Gerve et al; "Condensation of Glyoxal with Triethylenetetraamine. Stereochemistry, Cyclization and Deprotection"; Tetrahedron LETT., vol. 40, 1999, pp. 2517–2520, XP002175526.

Ferrari et al; "A Pratical Synthesis of 1, 4, 7, 10–Tetraazacyclododecane, A Pivotal Precursor for MRI Contrast Agents" Synthetic Communication, vol. 30, No. 1, 2000, pp. 15–21, XP001012734.

Brown et al, "Selective Reductions. 29. A Simple Technique To Achieve an Enhanced Rate of Reduction of Representative Organic Compounds by Borane–Dimethyl Sulfide", *J. Org. Chem*. 1982, vol. 47, No. 16, pp. 3153–3163.

* cited by examiner

Primary Examiner—James O. Wilson
Assistant Examiner—Zachary C. Tucker
(74) Attorney, Agent, or Firm—Nixon & Vanderhye P.C.

(57) ABSTRACT

A process for the preparation of compound of formula (I A), decahydro-2a,4a,6a,8a-tetraazacyclopent[fg] acenaphthylene and the corresponding functionalized compounds of general formula (I), intermediates for the preparation of 1,4,7,10-tetraazacyclododecane (II A) and corresponding derivatives (II), by preparation of compounds of general formula (III) and subsequent reduction thereof.

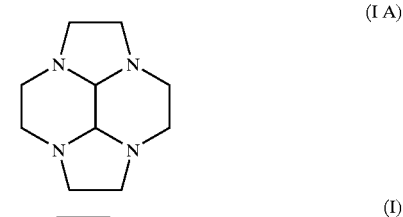

(I A)

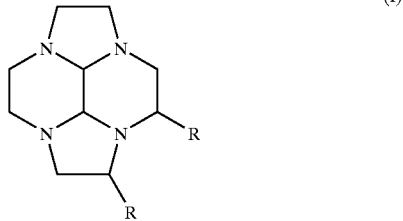

(I)

29 Claims, No Drawings

PROCESS FOR THE PREPARATION OF DECAHYDRO-2A,4A,6A,8A-TETRAAZACYCLOPENT[FG] ACENAPHTHYLENE AND FUNCTIONALIZED DERIVATIVES

This application was filed under 35 U.S.C. 371, and is the U.S. National Stage of PCT/EP01/04092, filed 10 Apr. 2001.

The present invention relates to a novel process for the preparation of the compound of formula (I A) decahydro-2a,4a,6a,8a-tetraazacyclopent-[fg]acenaphthylene, and of the corresponding functionalized compounds having formula (I),

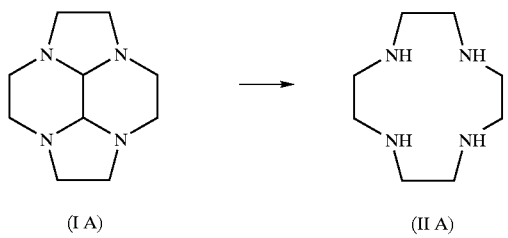

used for the preparation of 1,4,7,10-tetraazacyclododecane (II A)

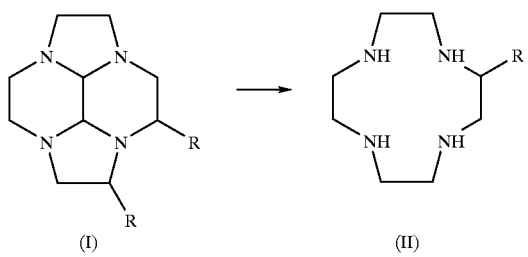

and of the related derivatives (II), through preparation and reduction of the compounds of general formula (III), comprising the steps shown in Scheme 1:

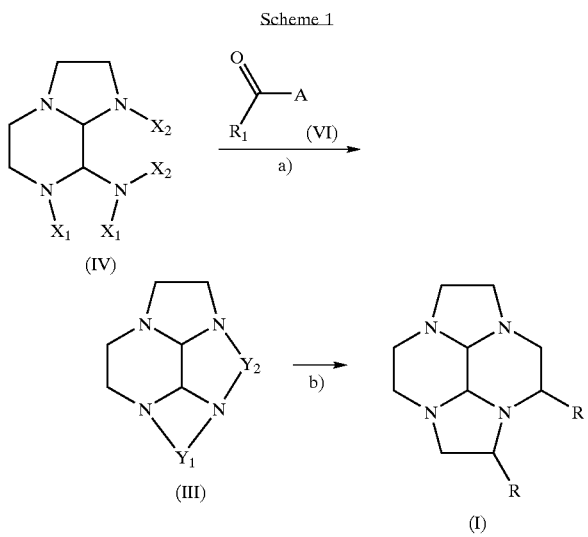

The preparation of 1,4,7,10-tetraazacyclododecane (commonly named Cyclen) (II A) according to the present invention is an alternative to the conventional procedure by Richman-Atkins (see for example J. Am. Chem, Soc., 96, 2268, 1974), which is at present industrially used for the production of compound (II A), in the form of the sulfate salt.

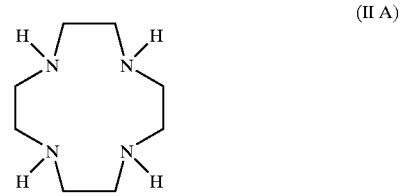

1,4,7,10-Tetraazacyclododecane is the precursor for the synthesis of macrocyclic chelating agents for metal ions.

In particular, the complexes of said chelants with paramagnetic metal ions, especially with the gadolinium ion, are characterized by high stability and can be used in the diagnostic field of the nuclear magnetic resonance technique.

Two gadolinium complexes, Dotarem® and Prohance®, at present commercially available and having a chemical structure based on Cyclen, as well as other complexes, are being studied.

It is therefore highly desirable to provide a process for the preparation of said intermediate which is advantageous both from the costs and environmental standpoints, avoiding for example the preparation of the amine tosyl derivatives commonly used in the conventional Richman-Atkins synthesis.

WO 97/49691 disclosed a process for the preparation of compound (II A) by the steps shown in Scheme 2, in which the compound of formula (I A), decahydro-2a,4a,6a,8a-tetraazacyclopent[fg]acenaphthylene, is the key intermediate for the formation of compound (II A), and is obtainable by cyclization of the intermediate (IV), octahydro-3H,6H-2a,5,6,8a-tetraazacenaphthylene, which can in its turn be prepared from triethylenetetramine and glyoxal.

In Scheme 2, Y is —OH (glyoxal hydrate) or [—SO$_3^-$ Na$^+$] (Bertagnini's salt) and X is halogen or a sulfonyloxy group

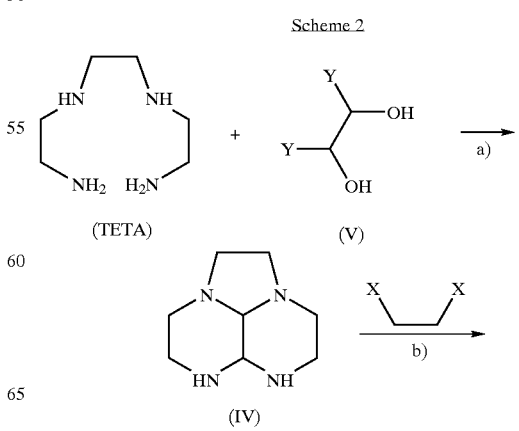

-continued

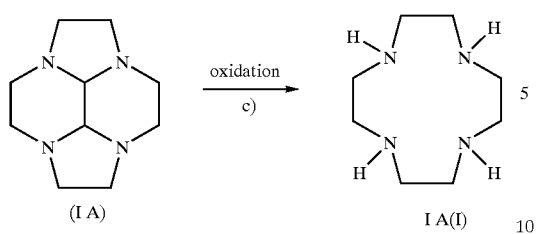 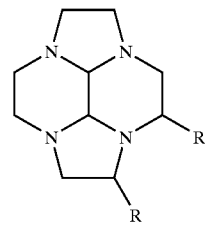

Said process has however some drawbacks. The use of a halogenated alkylating agent such as 1,2-dibromoethane or 1,2-dichloroethane (scheme 2, step a) in the condensation step, although not involving particular supplying problems, requires specific precautions during use. 1,2-Dichloroethane is in fact a cancerogenic, flammable compound which is used in strong excess in this process. This makes the recovery of the reaction solvent free from 1,2-dichloroethane difficult. Moreover the reaction yield is not very high.

Furthermore, ethylene glycol sulfonic esters have to be prepared, as they are not commercially available, and they involve the unavoidable production of wastes containing sulfonic acids (methanesulfonic, paratoluenesulfonic) which are to be discharged on industrial scale.

It has now surprisingly been found, and this is the object of the present invention, a process for the preparation of compounds of general formula (I), comprising the steps shown in Scheme 1

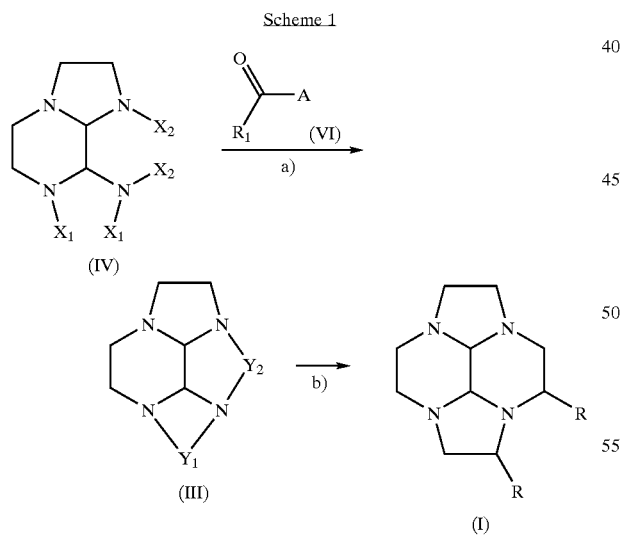

in which $X_1$, $X_2$, R, $R_1$, $R_2$ and A have the meanings shown below.

In particular, the process for the preparation of the compounds of general formula (I)

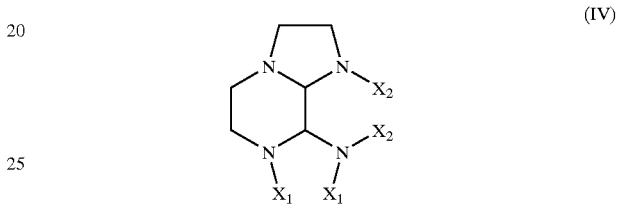

in which the groups R are both hydrogen, or one is hydrogen and the other is a straight or branched $C_1$–$C_4$ alkyl group, optionally substituted with one or more —OPg-protected hydroxy groups, in which Pg is a hydroxy-protecting group, comprises:

step a) reacting a compound of general formula (IV),

in which, when the groups $X_1$ are hydrogen, the groups $X_2$ form a —$CH_2$—$CH_2$— group, or vice versa, the groups $X_1$ are a —$CH_2$—$CH_2$— group when the groups $X_2$ are hydrogen, with a compound of general formula (VI)

(VI)

$$\underset{R_1}{\overset{O}{\|}}{-}A$$

in which A is a group of formula —$COR_1$ or —$CHRR_2$ wherein R has the meaning defined above, $R_1$ is halogen or $C_1$–$C_4$ alkoxy and $R_2$ is a leaving group such as halogen or sulfonyloxy, in at least unitary molar ratio, at a temperature above 50° C.;

step b) reducing the compounds obtained from step a), having general formula (III)

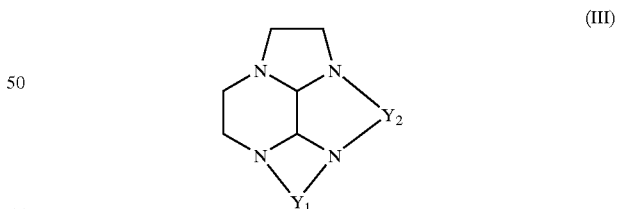

in which one of $Y_1$ or $Y_2$ is —$CH_2$—$CH_2$— and the other is —CO—CO— or a group of formula —COCHR, wherein R has the meaning defined above, in the presence of an amido-reducing agent.

The compounds of formula (I) resulting from the reduction reaction at step b) of Scheme 1, can conveniently be transformed into 1,4,7,10-tetraazacyclododecane derivatives (II A) having general formula (II), according to the procedure disclosed, for example, in WO 97/49691.

In the process shown in Scheme 1, compounds (IV) are prepared as described in WO 97/49691.

Step a) of Scheme 1 consists in condensing compounds (IV) with compounds (VI), operating under inert gas atmosphere (e.g. nitrogen), using at least 1 mol of compound (VI) per mol of compound (IV), at a temperature above 50° C., preferably in a range of 60 to 75° C.

The reaction can be carried out without solvent or in the presence of a solvent, which is preferably selected from: aromatic inert, aprotic dipolar or straight or branched $C_1$–$C_4$ alcohols and polyethers. Preferred solvents are selected from the group of: toluene, dimethylacetamide, dimethylformamide, N-methylpyrrolidone, DMSO, $C_1$–$C_4$ alcohols as defined above, glyme and diglyme. Alcohols are particularly preferred.

The reaction time ranges from 0.5 to 36 hours, depending on the solvent and the experimental conditions.

In a further aspect of the present invention, the process described in Scheme 1 can be carried out, without significantly changing the conditions described above, by using in step a) a catalyst which has a surprising effect on the progress of the reaction.

Significant decreases in reaction times and advantageous increases in yields are in fact obtained, as it will be shown in the experimental section.

Catalysts are selected from alkali or alkaline-earth metal salts of anions of straight or branched $C_1$–$C_4$ alcohols, or heterocyclic aromatic bases.

Said catalysts are preferably selected from the group consisting of sodium methoxide, sodium ethoxide or one of the compounds of formula:

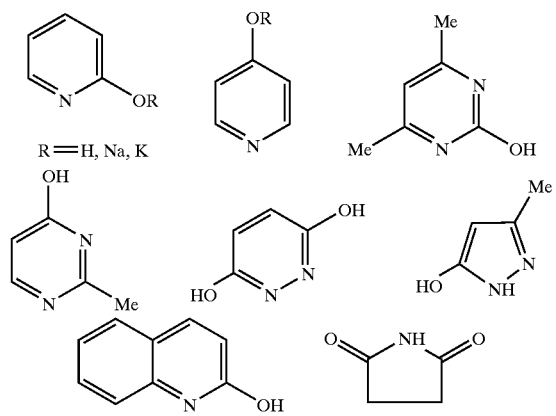

Sodium methoxide and 2-hydroxypirydine are particularly preferred and used in amounts ranging from 0.01 to 2 mol per mol of compound (IV).

Preferred compounds of formula (VI)

(VI)

are those in which:
when $R_1$ is a halogen or a methoxy or ethoxy group; then A is a group of formula —$COR_1$ in which $R_1$ is a halogen or a methoxy or ethoxy group, or a —$CHRR_2$ group in which R is as defined above and $R_2$ is a leaving group, such as a halogen or a sulfonyloxy group.

Particularly preferred are the compounds of formula (VI), in which:
when $R_1$ is methoxy, ethoxy, chlorine or bromine; A is a group of formula $COR_1$ or a $CHRR_2$ group, in which $R_1$ is chlorine, bromine, or a methoxy or ethoxy group; R is as defined above and $R_2$ is a leaving group, such as chlorine, bromine or a sulfonyloxy group.

The compounds of formula (VI) are preferably added in amounts ranging from one to four mol per mol of compound (IV).

The compounds of general formula (III) resulting from the condensation reaction at step a) of Scheme 1 can be isolated from the solution upon completion of the reaction, either in the salified form with an inorganic acid (e.g. halo acid) or as the free base, and can both be recovered with usual crystallization and/or precipitation techniques with organic solvents. Particularly suitable are, for example, n-hexane, toluene, methanol, ethanol and n-butanol.

Compounds (III) are preferably isolated in the salified form, as the hydrochloride, sulfate or phosphate salts.

At step b) of Scheme 1, compounds (III) are reduced to yield the compounds of general formula (I).

The reduction is carried out by using typical amido-reducing agents. The reaction is usually carried out in dry medium and under inert gas atmosphere. Examples of methods useful for the reduction of amides comprise the use of sodium bis(methoxyethoxy)aluminum hydride, $LiAlH_4$, $NaBH_4$ in the presence of other reagents, other hydrides and hydride complexes, the catalytic hydrogenation on platinum oxide and in solution of HCl, borane or its adducts with THF (tetrahydrofuran) or DMS (dimethylsulfide).

Sodium bis(methoxyethoxy)aluminum hydride, commercially known as Vitride® or Redal®, is preferred, as it is particularly effective.

The reduction reaction is generally carried out by adding compounds (III) to the solution containing the reducing agent, which is added as a 70% toluene solution, in amounts ranging from 3 to 4 mol per mol of compound (III), and at a reaction temperature ranging from 35° C. to the toluene reflux temperature.

The reduction reaction is preferably carried out at the reflux temperature of the solution for 1.3 hours, using at least 3 mol of sodium bis(methoxyethoxy)aluminum hydride in toluene solution per mol of compound (III).

Compound (I) resulting from the reduction reaction can be isolated either as the free base or salified, for example as hydrochloride or phosphate.

The use of sodium bis(methoxyethoxy)aluminum hydride, compared with $LiAlH_4$ and related hydrides, provides advantages both in terms of safety and costs of the reduction reaction: in fact, it is not pyrophoric, does not react with oxygen and is highly soluble in a number of solvents, such as aromatic hydrocarbons and ethers, which makes it easy to use it and to carry out the reduction reaction in more concentrated solutions.

At the end of the reduction, compound (I) is recovered with the usual extraction, crystallization and/or precipitation techniques, thus removing the aluminum inorganic salts formed during the reaction.

A particularly effective isolation procedure of compound (I), also when applied on the industrial scale, consists in using a strong cationic ion resin to temporarily bind the product on the resin, from which it is subsequently eluted with an ammonia aqueous solution.

A strong cationic resin, such as Amberjet® 1200, suitably regenerated in the acidic form, or an equivalent commercial resin, is preferably used.

The process of the invention is particularly useful for the preparation of compound (I A) shown in the following Scheme 3.

Scheme 3

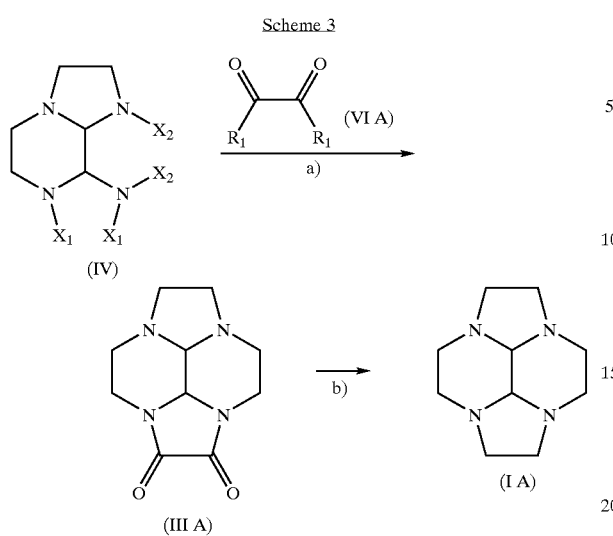

in which
R$_1$ is C$_1$–C$_4$ alkoxy and compound (VI A) is added in amounts of at least 1 mol per mol of compound (IV).

Compound (I A) can conveniently be transformed into 1,4,7,10-tetraazacyclododecane (II A) or the corresponding derivative, with the procedure described in WO 96/28432, or that in WO 98/49151, and preferably as disclosed in WO 00/53588, by hydrolysis with diethylenetriamine in water, at pH ranging from 5 to 9, at a temperature ranging from 90 to 120° C., in the presence of 5–10 mol of diethylenetriamine per mol of (I A), under inert gas atmosphere or in the air, for 12–48 h, isolating compound (II A) as the tetrahydrochloride.

Compounds of formula (VI A), in which R$_1$ is methoxy or ethoxy are preferred. Particularly preferred is diethyl oxalate, which is added in amounts of at least 1 mol per mol of compound (IV), preferably in absolute ethanol as reaction solvent and at a temperature of 60–70° C., for a total reaction time ranging from 6 to 24 hours.

Furthermore, the process shown in the following Scheme 4 is particularly preferred.

Scheme 4

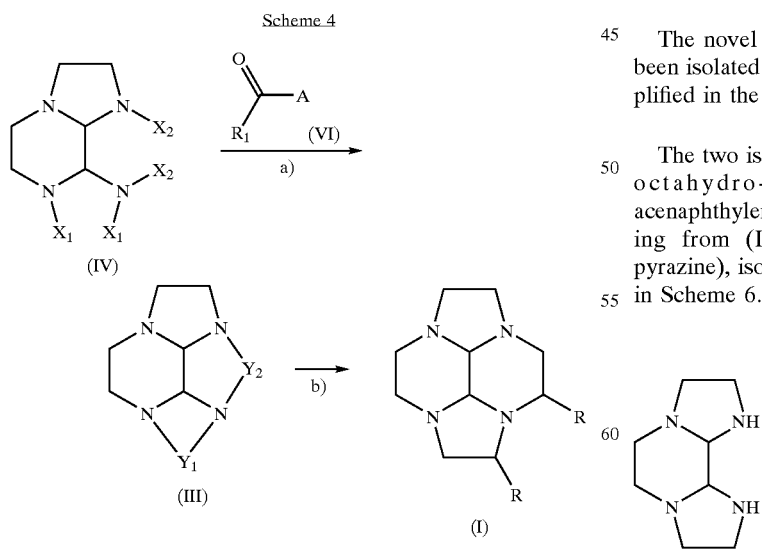

in which R$_1$ is C$_1$–C$_4$ alkoxy and A is a —CHRR$_2$ group wherein R and R$_2$ have the meanings defined above.

Particularly preferred in step a) of Scheme 4 is the use of compounds (VI), in which R$_1$ is ethoxy or methoxy and A is a group of formula —CHRR$_2$ in which R is H and R$_2$ is Cl or Br.

Particularly preferred is the use of ethyl chloroacetate as compound (VI), in amounts of at least 1 mol per mol of compound (IV), in absolute ethanol, at a temperature from 50 to 70° C., in the presence of at least 1 mol of Na$_2$CO$_3$ and at least 0.02 mol of NaI per mol of compound (IV) and for a reaction time from 3 to 36 hours.

A further object of the invention is the preparation of both stereoisomers of formulae (VII) and (VIII), cis and trans octahydro-2a,4a,6a,8a-tetraazacyclopent[fg]acenaphthylene-1,2-dione, as shown in Scheme 5.

Scheme 5

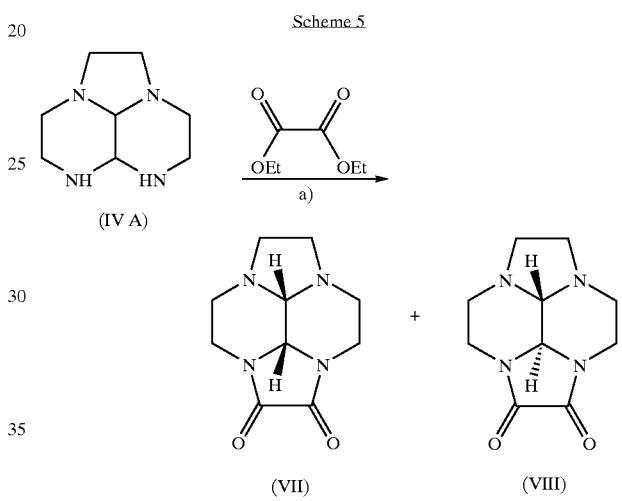

Compound (IV A), prepared as described above, is reacted using in step a) the general conditions described above and diethyl oxalate as reagent.

The novel compounds of formula (VII) and (VIII) have been isolated and characterized by X ray analysis, as exemplified in the experimental section.

The two isomers of formulae (IX) and (X), cis and trans octahydro-2a,4a,6a, 8a-tetraazacyclopent[fg]acenaphthylene-3,4-dione, are prepared analogously, starting from (IV B) (decahydro-diimidazo-[1,2-a:2',1'-c] pyrazine), isomer of (IV A), with diethyl oxalate, as shown in Scheme 6.

Scheme 6

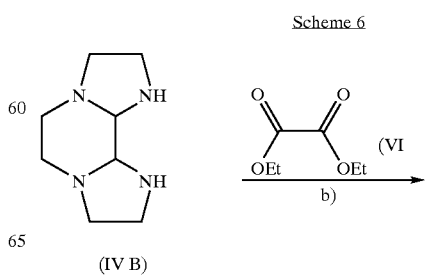

-continued

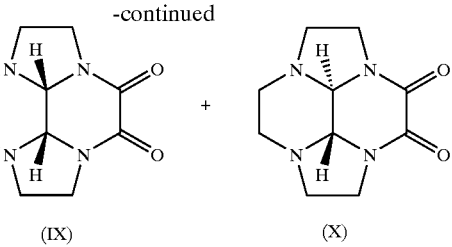

(IX)   (X)

In this case also the compounds have been recovered and characterized by X ray analysis.

Compound (IX) is already known in literature, whereas compound (X) is novel.

Literature (see G. Hervè, H. Bernard, Tetrahedron Lett., 40. 2517–2520. 1999) described the condensation reaction of glyoxal with triethylenetetramine, the subsequent cyclization reaction with 1,2-dibromoethane to give compound (I A) and the deprotection to 1,4,7,10-tetrazacyclododecane (II A). The cited paper also reports the $^{13}$C-NMR spectra of the mixtures of the (IV A) and (IV B) cis and trans stereoisomers,

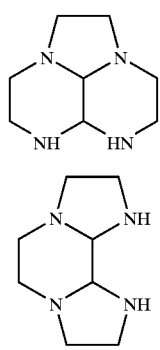

(IV A)

(IV B)

and the conversion conditions of the corresponding isomers at different temperatures and experimental conditions.

The same Authors (G. Hervè, H. Bernard et al. Eur. J. Org. Chem., 33–35, 2000) reported the preparation of compound (IX) by condensation of (IV B) with diethyl oxalate in ethanol at room temperature as single isomer, whose stereochemistry is established by X rays.

It is also reported that the condensation of compound (IV C) with diethyl oxalate

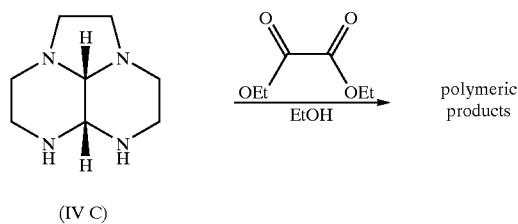

(IV C)

under the same conditions does not take place and prolonged heating of the solution causes polymeric products to form.

In conclusion, the process of the invention, notwithstanding the contrary teaching found in literature, provides in good yield compounds (VII) and (VIII) starting from (IVA), and compounds (IX) and (X) starting from (IVB). Furthermore, by the process of the invention it is possible to isolate and characterize the novel compounds (VII), (VIII) and (X).

A further object of the invention is the process for the preparation of compounds (VII) and (VIII) starting from (IV C) as shown in the following Scheme 7.

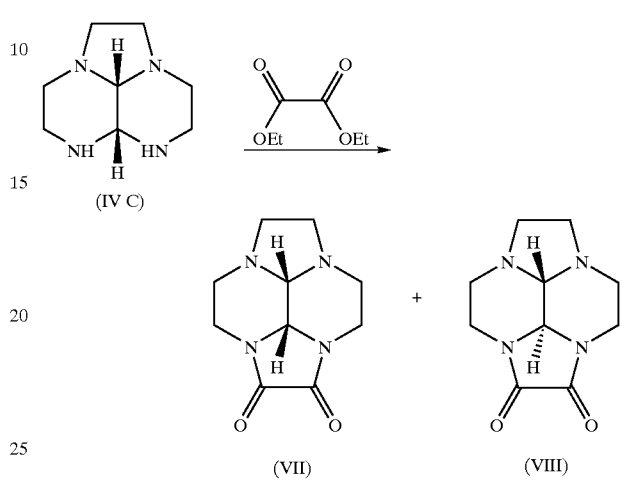

(VII)   (VIII)

by condensation with diethyl oxalate, even at temperatures below 50° C.

A further object of the invention are compounds of formula (III)

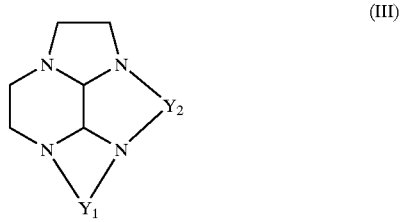

(III)

wherein one of $Y_1$ and $Y_2$ is —$CH_2$—$CH_2$— and the other is —CO—CO— or a group of formula —CO—CHR—, in which R is H, straight or branched $C_1$-$C_4$ alkyl, optionally substituted with one more —OPg-protected hydroxy groups in which Pg is a conventional hydroxy-protective groups, preferably benzyl.

Preferred compounds of formula (III) are the compounds of formula (XII) and (XIII)

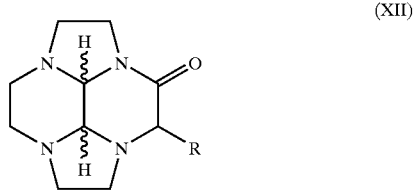

(XII)

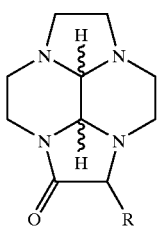

(XIII)

in which R is H, straight or branched $C_1$–$C_4$ alkyl, or a phenylmethoxymethyl group (R=PhCH$_2$OCH$_2$—).

Particularly preferred are compounds (VII), cis-octahydro-2a,4a,6a,8a-tetraazacyclopent[fg] acenaphthylene-1,2-dione, (VIII) trans octahydro-2a,4a,6a,8a-tetraazacyclopent[fg]acenaphthylene-1,2-dione, (X) trans octahydro-2a,4a,6a,8a-tetraazacyclopent[fg] acenaphthylene-3,4-dione,

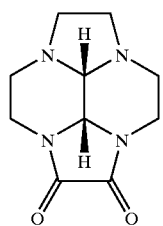

(VII)

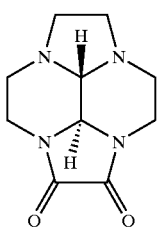

(VIII)

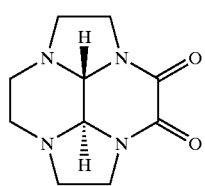

(X)

(XII A) decahydro-2a,4a,6a,8a-tetraazacyclopent[fg] acenaphthylene-3-one, (XIII A) decahydro-2a,4a,6a,8a-tetraazacyclopent[fg]-acenaphthylene-1-one and (XIII B) 2-(phenylmethoxymethyl)-decahydro-2a,4a,6a,8a-tetraazacyclopent[fg]acenaphthylene-1-one.

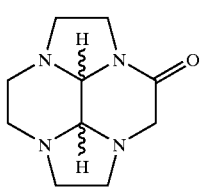

(XII A)

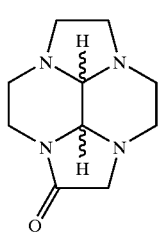

(XIII A)

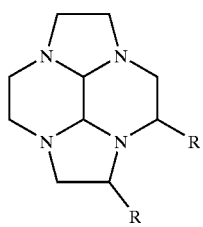

(XIII B)

A further object of the invention are the compounds of formula (I),

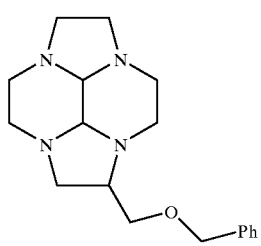

(I)

in which the groups R are both H or one is hydrogen and the other is straight or branched $C_1$–$C_4$ alkyl, optionally substituted with one or more —OPg-protected hydroxy groups, in which Pg is a hydroxy-protective group.

Particularly preferred is the compound of formula (I B)

(I B)

2-phenylmethoxymethyldecahydro-2a,4a,6a, 8a-tetraazacyclopent[fg]-acenaphthylene, in which R is the phenylmethoxymethyl group (R=PhCH$_2$OCH$_2$—).

A further object of the present invention is the compound of formula (XI), trans-decahydro-2a,4a,6a,8a-tetraazacyclopent[fg]acenaphthylene.

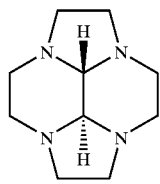

(XI)

The following examples illustrate the best experimental conditions to carry out the process of the invention.

EXPERIMENTAL SECTION

The following procedure was used for the gas-chromatographic analysis:

| | |
|---|---|
| Instrumentation | Hewlett-Packard 5890 gas-chromatographic system, equipped with autosampler series 7673 and HP-3365 unit. |
| Column | CP Sil 19 CB, 25 m × 0.32 mm, 0.52 mm film |
| Oven temp. program: | first isotherm at 120° C. for 5 min; ramp 15° C./min to 260° C.; second isotherm at 260° C. for 12 min |
| Injector | Split flow rate 11.5 mL/min<br>Temperature 250° C. |
| Detector | FID<br>Temperature 275° C.<br>Hydrogen pressure 1.2 bars<br>Air pressure 2.8 bars |
| Column flow rate | 1.2 µl/min |
| Carrier gas | He$_2$<br>Column pressure 20 psi<br>Auxiliary gas flow rate 10 mL/min<br>Septum purge flow rate 5 mL/min |
| Injection | 1 µl |
| Sample concentration | 20 mg/mL |
| Internal standard | Acenaphthene |
| Internal standard concentr.: | 10 mg/mL |

EXAMPLE 1

Preparation of cis/trans of octahydro-2a,4a,6a,8a-tetraazacyclopent[fg]acenaphthylene-1,2-dione (III)

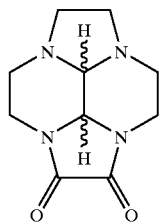

(III)

A) Preparation of 3H,6H-2a,5,6,8a-octahydrotetraaza-acenaphthylene (IV A)

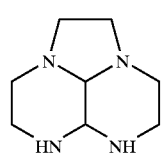

(IV A)

A suitable reactor is loaded, under mild nitrogen stream, with 370.5 g of straight hydrated triethylenetetramine (TETA), 2 kg of water and 296.4 g of calcium hydroxide. Then a 9% (w/w) glyoxal aqueous solution prepared by mixing 290 g of 40% solution with 1 kg of water, stirred in nitrogen blanket and cooled to 0–5° C., is added to the resulting suspension. After completion of the addition, the mixture is kept at 5° C. for 1 h, and filtered through Celite® previously washed with 0.5 kg of water. The filtrate is evaporated to dryness under reduced pressure.

The product is not subjected to purification but is directly used for the subsequent reaction.

Yield: 98.5% (on dry matter)

GC assay: >75% (% area)

B) Preparation of Compound (III) and Isolation as Hydrochloride

Into a 1 L reactor, kept in nitrogen atmosphere and containing a solution of 50 g (0.297 mol) of compound (IV) prepared as described in example 1A) in 0.4 L of ethanol, 130 g (0.891 mol) of diethyl oxalate are added. The resulting solution is kept under magnetic stirring at 68° C. for 24 hours, then partially concentrated under reduced pressure to 384 g. 86.4 g (0.296 mol) of a 12.5% w/w HCl ethanol solution are dropped into the reaction mixture and kept under magnetic stirring for 40 minutes. The suspension is kept for 45 minutes under magnetic stirring and the resulting solid is filtered and washed on the filter with 75 mL of ethanol. The humid solid is dried in a static dryer under vacuum at 40° C. for 12 hours, to obtain 38.4 g (0.146 mol) of the desired compound with the following analytical characteristics:

GC assay: 94.6% (% area)

Recovery yield: 49%

The $^1$H-NMR, $^{13}$C-NMR, IR and MS spectra are consistent with the indicated structure.

EXAMPLE 2

Preparation of Compound (III), Free Base

In a suitable reactor, in nitrogen atmosphere, a solution of 50.5 g (0.3 mol) of compound (IV) prepared as described in example 1A) in 0.4 L of ethanol and 131.5 g (0.9 mol) of diethyl oxalate are loaded. The solution is heated to 68° C. and kept under magnetic stirring at this temperature for 27 hours. The solvent is evaporated off under reduced pressure to a residue weighing 150 g, and a solution of 123 mL of toluene and 13 mL of ethanol is added. The resulting suspension is kept under magnetic stirring for 2 hours, then filtered through porous septum. The solid is washed with 40 mL of an ethanol/toluene=1/1 solution (v/v), then dried in a static dryer under vacuum at 40° C. for 12 hours, to obtain 31 g (0.132 mol) of the desired compound having the following analytical characteristics:

GC assay: 95% (% area)

Yield: 44%

The $^1$H-NMR, $^{13}$C-NMR, IR and MS spectra are consistent with the indicated structure.

EXAMPLE 3

Preparation of Compound (III) by Reaction in Mass

Into a 50 mL round-bottom flask equipped with reflux condenser, thermometer and mechanical stirrer, kept in nitrogen atmosphere, 12 g (0.071 mol) of product prepared as in example 1 A) and 11.9 g (0.078 mol) of diethyl oxalate are loaded. The mixture is heated in mass at 65° C. for 5 hours, then added with 1.19 g (0.0078 mol) of diethyl oxalate and heating is continued for 6 hours. The mixture is left to cool to room temperature and the ethanol formed during the reaction is distilled off under partial vacuum. The product is purified by chromatography on a silica gel column (eluent: $CHCl_3$/methanol=8/2 V/V), to obtain 11.2 g (0.050 mol) of the desired compound having the following analytical characteristics:

GC assay: 98 (% area)

Yield: 60%

EXAMPLE 4

Preparation of Compound (III) in the Presence of 2-hydroxypirydine

Into a solution of 50.5 g (0.3 mol) of compound (IV) prepared as described in example 1A) in 0.4 L of ethanol, under magnetic stirring and nitrogen atmosphere, 14.1 g (0.148 mol) of 2-hydroxypyridine and 86.80 g (0.594 mol) of diethyl oxalate are added. The solution is kept at 68° C. for 6 hours, then partially concentrated, under vacuum partial, to a weight of 122 g.

The residual product is added with 170 mL of toluene and 18 mL of ethanol and the suspension is kept under magnetic stirring for 17 hours, then filtered and washed on filter with an ethanol/toluene 1/1 solution (v/v). The product is dried in a static dryer to obtain 41 g (0.179 mol) of the desired compound having the following analytical characteristics:

GC assay: 96.9%

Yield: 60%

The $^1$H-NMR, $^{13}$C-NMR, IR and MS spectra are consistent with the indicated structure.

EXAMPLE 5

Preparation of Compound (III) in the Presence of Sodium Methoxide

In a solution of 53.5 g (0.318 mol) of compound (IV) in 0.4 L of ethanol, under magnetic stirring and nitrogen atmosphere, 17.2 g (0.318 mol) of sodium methoxide are added. The suspension is stirred until complete dissolution, and then is added 92.9 g, (0.636 mol) of diethyl oxalate. The mixture is heated to 68° C. and kept at this temperature for 1.5 hours. The solution is partially concentrated and then 130 mL ethanol is added to the residue at 70° C.

The resulting suspension is kept for 72 hours under mechanical stirring at 23° C. The solid product is filtered, washed with 45 mL of ethanol and dried in a static dryer under partial vacuum to obtain 35.3 g of the desired compound (0.159 mol) having the following analytical characteristics:

G.C. assay: 95%

Yield: 50%

The $^1$H-NMR, $^{13}$C-NMR, IR and MS spectra are consistent with the indicated structure.

EXAMPLE 6

Preparation of (VII) cis octahydro-2a,4a,6a,8a-tetraazacyclo-pent[fg]-acenaphthylene-1,2-dione

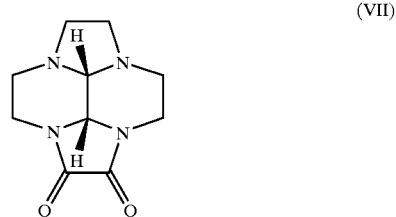

(VII)

The intermediate of formula (IV A), obtained as described in preparation 1A), is purified through salification as acetate, according to the following procedure:

15 g (0.09 mol) of compound prepared as described in preparation 1A) are dissolved in 100 g of toluene, then 5.5 g of conc. acetic acid solution are dropped into the solution and the resulting suspension is stirred for 10 minutes. The resulting solid is filtered, washed with toluene, and dried under vacuum at 30° C. to obtain 14.1 g of compound (IV C) as monoacetate.

GC assay: 98% (% area)

Recovery yield: 70%

2 g of the above prepared compound are dissolved in a 10% NaOH solution and extracted with chloroform. The separated organic phase is dried, filtered and evaporated to a residue weighing 1 g (0.006 mol), which is dissolved in 10 mL of ethanol and added with 2.6 g (0.018 mol) of diethyl oxalate. The resulting solution is heated at 70° C. for 12 hours and concentrated under vacuum to a solid residue. The crude product is purified by silica gel chromatography, using a $CHCl_3$/MeOH=8/2 eluent mixture (v/v), to obtain 0.6 g of compound (VII) having the following analytical characteristics:

GC assay: 99 (% area)

The $^1$H-NMR, $^{13}$C-NMR, IR and MS spectra are consistent with the indicated structure.

EXAMPLE 7

Preparation of Compounds (VII) and (VIII), cis and trans octahydro-2a,4a,6a,8a-tetraazacyclopent[fg] acenaphthylene-1,2-dione

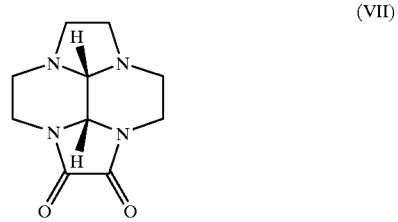

(VII)

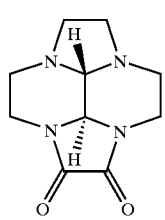

(VIII)

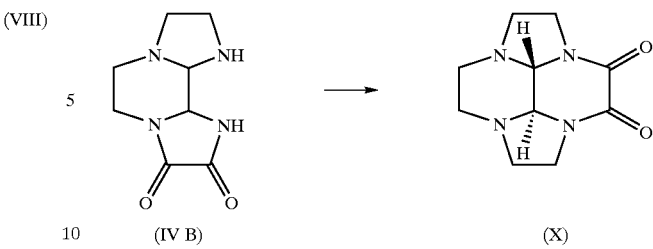

A) Preparation of (VII) cis octahydro-2a,4a,6a,8a-tetraazacyclopent[fg]-acenaphthylene-1,2-dione.

In a 1 L reactor, in nitrogen atmosphere, 160 mL of absolute ethanol, 21 g (0.125 mol) of product prepared as in example 1 A), 6.74 g (0.125 mol) of sodium methoxide and 36.5 g (0.250 mol) of diethyl oxalate are loaded. The solution is heated and kept at 68° C. for 2 hours, then cooled to room temperature and 12.3 g of a 37% HCl solution (0.125 mol) are dropped therein. The resulting suspension is filtered through Celite and the filtrate is evaporated to dryness to give crude compound (VIII), which will be used for the subsequent isolation of (VIII) (see part B).

The product on the filter is suspended in deionized water and filtered through Celite. In the filtrate 6.9 g (0.065 mol) of $Na_2CO_3$ are added and the resulting suspension is evaporated to a residue. The solid residue is suspended in methanol and filtered at 60° C. The resulting solution is left to spontaneously cool to 23° C. and the solid product obtained from the crystallization is filtered and dried under vacuum at 40° C. for 12 hours, to obtain 7.5 g of dry product having the following analytical characteristics:

GC assay: 100 (% area)

The $^1$H-NMR, $^{13}$C-NMR, IR, MS and the solid state structure obtained by X ray diffractometry are consistent with the indicated structure.

B) Isolation of (VIII) trans octahydro-2a,4a,6a,8a-tetraazacyclopent[fg]-acenaphthylene-1,2-dione Crude compound (VIII) (see A) is purified by silica gel chromatography using a $CHCl_3$/MeOH/$NH_3$ eluent mixture. The fractions containing the purified product are combined and evaporated to a solid residue. The resulting product is recrystallized from methanol to obtain a product, which is dried under vacuum at 40° C. for 12 hours to yield 1.5 g of compound having following analytical characteristics:

GC assay: 100 (% area)

The $^1$H-NMR, $^{13}$C-NMR, IR, MS and the solid state structure obtained by X ray diffractometry are consistent with the indicated structure.

EXAMPLE 8

Preparation and Isolation of (X) trans octahydro-2a,4a,6a,8a-tetraazacyclopent[fg]acenaphthylene-3,4-dione A) Preparation of decahydro-diimidazo-[1,2-a:2',1'-c] pyrazine (IV B)

In a suitable 2 L reactor, maintained under nitrogen atmosphere, 50 g (305 mmol) of straight hydrated TETA and 1 L of absolute ethanol are loaded. To the solution 44.5 g (305 mmol) of a 40% glyoxal solution are added. After completion of the addition, the solution is kept under magnetic stirring at 23° C. for 17 hours. The resulting solution is concentrated under partial vacuum to an oily residue.

GC assay: 75% (% area)

B) Preparation and Isolation of Compound (X)

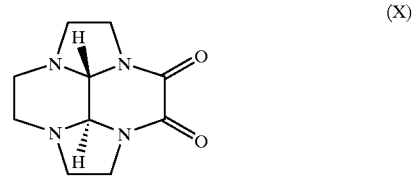

(X)

In a 0.25 L round-bottom flask equipped with mechanical stirrer and thermometer, under nitrogen atmosphere, 5.5 g (0.0326 mol) of compound (IV B) prepared as described above in Example 8 A), 80 mL of absolute ethanol, 0.88 g (0.0163 mol) of sodium methoxide and 2,38 g (0.0163 mol) of diethyl oxalate are loaded. The resulting solution is heated at 68° C. for 8 hours and, after partial concentration under vacuum, is left to spontaneously cool to 23° C. The crystallized solid product is filtered and recrystallized from methanol. The product is recrystallized, filtered and dried under vacuum in a static dryer at 40° C. for 12 hours, to yield 0.5 g of the desired compound having the following analytical characteristics:

GC assay: 100 (% area)

The $^1$H-NMR, $^{13}$C-NMR, IR, MS and the solid state structure obtained by X ray diffractometry are consistent with the indicated structure.

EXAMPLE 9

Preparation and Isolation of (IX) cis octahydro-2a,4a,6a,8a-tetraazacyclopent[fg]acenaphthylene-3,4-dione

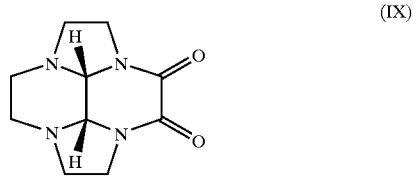

(IX)

In a 1 L reactor equipped with mechanical stirrer, thermometer, reflux condenser and nitrogen blanket, 30 g (0.178 mol) of product prepared as in example 8 A), 225 mL of absolute ethanol and 13 g (0.089 mol) of diethyl oxalate are loaded. The solution is heated and kept at 68° C. for 18 hours, and then 2.6 g (0.0178 mol) of diethyl oxalate are added and the solution is kept at 68° C. for 4 hours. The solution is left to cool to 23° C. and the crystallized solid is filtered and recrystallized from methanol. The resulting product is dried at 40° C. for 12 hours to a weight of 6.2 g (0.0279 mol) and has the following analytical characteristics:

GC assay: 100 (% area)

The $^1$H-NMR, $^{13}$C-NMR, IR, MS and the solid state structure obtained by X ray diffractometry are consistent with the indicated structure.

EXAMPLE 10

Preparation of decahydro-2a,4a,6a,8a-tetraazacyclopent[fg]acenaphthylene-1-one (XIII A)

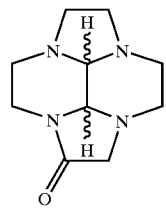
(XIII A)

In a 1 L round-bottom flask containing 0.2 L of ethanol and 18 g (0.107 mol) of compound (IV A) prepared as in example 1 A, are loaded 22.7 g (0.214 mol) of $Na_2CO_3$, 1.6 g (0.0107 mol) of NaI and 26.2 g (0.214 mol) of ethyl chloroacetate. The resulting suspension is stirred for 24 hours at 23° C., then filtered through porous septum and the resulting filtrate is evaporated to dryness.

In a 0.25 L round-bottom flask equipped with mechanical stirrer, reflux condenser and nitrogen blanket and thermometer, are placed 16 g of the above prepared product, 60 mL of ethanol, and 1.47 g of 2-pyrydinol (0.016 mol). The resulting solution is refluxed for 48 hours. The solution is cooled and evaporated to dryness. The residue is purified by silica gel chromatography with a $CHCl_3$/MeOH=95/5 (v/v) eluent solution. The fractions containing the purified product are combined and concentrated under partial vacuum to a solid residue, to obtain 10 g of purified compound having the following analytical characteristics:

Yield 45%

GC assay: 80 (% area)

EXAMPLE 11

Preparation of 2-(phenylmethoxymethyl)-decahydro-2a,4a,6a,8a-tetraazacyclopent[fg]acenaphthylene-1-one (XIII B)

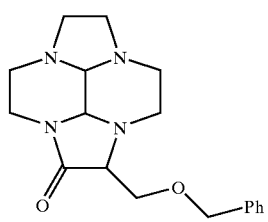
(XIII B)

In a 250 mL round-bottom flask 100 mL of ethanol and 10 g (0.059 mol) of compound (IV A) prepared as in example 1A are loaded, then 6.25 (0.059 mol) of sodium carbonate, 0.45 g (0.03 mol) of NaI and 21.4 g (0.088 mol) of ethyl 3-benzyloxy-2-chloro-propionate are added. The suspension is stirred for 36 hours at room temperature, then filtered. The solid is washed with 30 mL of ethanol. The filtrate is partially concentrated to 120 g and added with 2.66 (0.029 mol) of 2-pyrydinol. The resulting solution is refluxed for 48 hours, then evaporated and the residue is purified by silica gel chromatography, eluting with chloroform/methanol=9/1. The fractions containing the purified product are combined and evaporated to a residue, to obtain 7.4 g of compound.

The $^1$H-NMR, $^{13}$C-NMR, IR and MS spectra are consistent with the indicated structure.

EXAMPLE 12

Preparation of decahydro-2a,4a,6a,8a-tetraazacyclopent[fg]acenaphthylene (I A)

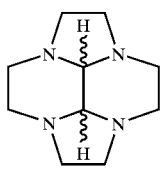
(I A)

In a 1 L round-bottom flask containing 100.8 g (70% in toluene; 0.349 mol) of Vitride® in 0.2 L of toluene, kept in nitrogen atmosphere and magnetic stirring, are added 19.4 g (0.087 mol) of compound (III), prepared as in example 5. The resulting suspension is heated and kept at 112° C. for 1 hour.

The solution is left to cool to 22° C., then 58 mL of a 5% w/w NaOH aqueous solution are slowly dropped therein. The two resulting phases are separated and the aqueous phase is extracted with toluene. The first separated organic phase and those deriving from the toluene extraction are combined, evaporated to dryness, and the residue is dissolved in 80 mL of deionized water. The aqueous solution is percolated onto a column containing 165 mL of Amberjet 1200® cationic resin, previously regenerated in the H⁺ form. Water is at first percolated on the resin bed to neutral eluate, and then a 2.5% $NH_4OH$ solution is percolated. The ammonia fractions containing the product are evaporated to dryness. The solid residue is extracted at 50° C. with n-hexane and the resulting solutions are combined and further evaporated under partial vacuum to a residue. The resulting solid product is dried in the presence of $P_2O_5$ to obtain 14.2 g (0.073 mol) of compound having the following analytical characteristics:

Tit. G.C.: 100%

Yield: 84%

The $^1$H-NMR, $^{13}$C-NMR, IR and MS spectra are consistent with the indicated structure.

EXAMPLE 13

Preparation of decahydro-2a,4a,6a,8a-tetraazacyclopent[fg]acenaphthylene (IA) starting from decahydro-2a,4a,6a,8a-tetraazacyclo-pent[fg]acenaphthylene-1-one (XIII A)

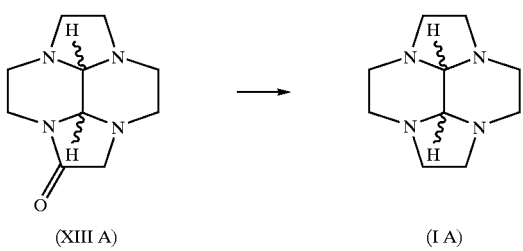

(XIII A)  (I A)

In a 0.1 L round-bottom flask containing 10 mL of toluene and 2.8 g (70% toluene; 0.0096 mol) of Redal®, maintained under mechanical stirring and nitrogen blanket, 1 g (0.004 mol) of the compound of example 10 is added at 45° C. The solution is heated to 100° C. for 1 hour, then cooled to room temperature and added with 1.5 mL of 5% NaOH. The two resulting phases are separated and the aqueous phase is extracted with toluene. The combined organic phases are concentrated under vacuum to a solid residue. The resulting product is purified by silica gel chromatography eluting with a CHCl$_3$/MeOH=8/2 mixture (v/v). The fractions containing the purified product are combined and concentrated to a solid residue weighing 0.60 g.

Yield: 77%

GC assay: 100 (% area)

The $^1$H-NMR, $^{13}$C-NMR, IR and MS spectra are consistent with the indicated structure.

EXAMPLE 14

Preparation of 2-phenylmethoxymethyl-decahydro-2a,4a,6a,8a-tetraazacyclo-pent[fg] acenaphthylene

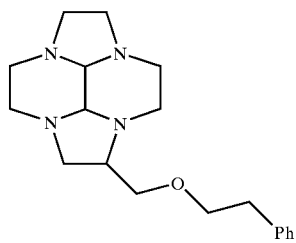

(I B)

Compound (I B) is obtained by using compound (XIII B) as starting product and the reductive conditions as described in example 13.

The $^1$H-NMR, $^{13}$C-NMR, IR and MS spectra are consistent with the indicated structure.

EXAMPLE 15

Preparation of trans-decahydro-2a,4a,6a,8a-tetraazacyclopent[fg]acenaphthylene (XI)

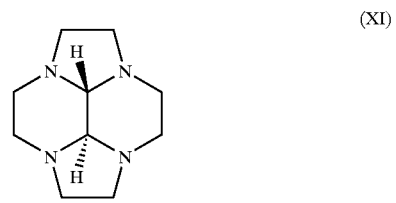

(XI)

Compound (XI) is isolated from the isomeric cis/trans mixture obtained from example 12, by silica gel chromatography, eluting with CHCl$_3$/CH$_3$OH=9:1. The resulting compound has the following analytical characteristics:

GC assay: 100 (% area)

The $^1$H-NMR, $^{13}$C-NMR, IR and MS spectra are consistent with the indicated structure.

What is claimed is:

1. A process for the preparation of the compounds of general formula (I)

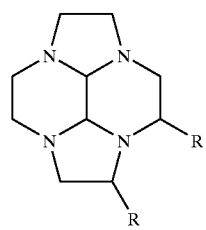

(I)

in which the groups R are both hydrogen, or one is hydrogen and the other is a straight or branched C$_1$–C$_4$ alkyl group, optionally substituted with one or more —OPg-protected hydroxy groups, in which Pg is a hydroxy-protecting group, which process comprises:

step a) reacting a compound of general formula (IV),

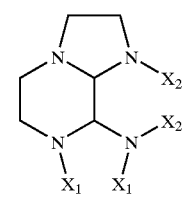

(IV)

in which, both of the groups X$_1$ are hydrogen or both are CH$_2$ and both of the groups X$_2$ are hydrogen or both are CH$_2$, provided that when the groups X$_1$ are hydrogen, the groups X$_2$ form a —CH$_2$CH$_2$— and when the groups X$_1$ are a —CH$_2$CH$_2$— group, then the groups X$_2$ are hydrogen, with a compound of general formula (VI)

(VI)

in which A is a group of formula —COR$_1$ or —CHRR$_2$ wherein R has the meaning defined above, R$_1$ is halogen or a C$_1$–C$_4$ alkoxy group and R$_2$ is a leaving group such as halogen or sulfonyloxy, in at least unitary molar ratio, at a temperature above 50° C.;

step b) reducing the compounds obtained from step a), having general formula (III)

(III)

in which one of $Y_1$ or $Y_2$ is —$CH_2$—$CH_2$— and the other is —CO—CO— or a group of formula —COCHR, wherein R has the meaning defined above, in the presence of an amido-reducing agent.

2. A process as claimed in claim 1 wherein in the compounds of formula (III), R is H or straight or branched $C_1$–$C_4$ alkyl, optionally substituted with one or more —OPg groups in which Pg is benzyl.

3. A process as claimed in claim 1 wherein the reaction of compound of formula (IV) with compound of formula (VI) is carried out under inert gas atmosphere, using at least 1 mol of compound (VI) per mol of compound (IV), in the presence of a solvent selected from: aromatic inert, aprotic dipolar, or straight or branched $C_1$–$C_4$ alcohols and polyethers.

4. A process as claimed in claim 3, wherein the solvent is selected from the group consisting of: toluene, dimethylacetamide, dimethylformamide, N-methylpyrrolidone, DMSO, $C_1$–$C_4$ alcohols, glyme and diglyme.

5. A process as claimed in claim 1, wherein the reactants are not dissolved in a reaction solvent.

6. A process as claimed in claim 1, in which step a) is carried out in the presence of alkali or alkaline-earth metal salts of anions of straight or branched $C_1$–$C_4$ alcohols, or of heterocyclic aromatic bases, as catalysts.

7. A process as claimed in claim 1, in which step a) is carried out in the presence of a catalyst selected from the group consisting of sodium methoxide, sodium ethoxide, or one of the compounds of formulae:

R=H, Na, K

8. A process as claimed in claim 7, wherein the catalyst is sodium methoxide or 2-hydroxypyridine, in amounts ranging from 0.01 to 2 mol per mol of compound (IV).

9. A process as claimed in claim 1, wherein compound of formula (III) is recovered upon completion of the reaction, either as a salt with an inorganic acid selected from the group consisting of hydrochloric, sulfuric and phosphoric acids, or as the free base.

10. A process as claimed in claim 1, wherein the reduction of compound (III) is carried out in dry medium and under inert atmosphere, using the amido-reducing agent selected from the group consisting of: sodium bis(methoxyethoxy) aluminum hydride, $LiAlH_4$, $NaBH_4$, borane or the tetrahydrofuran or dimethyl sulfide adducts thereof or by catalytic hydrogenation on platinum oxide and in HCl solution.

11. A process as claimed in claim 10, wherein are used sodium bis(methoxyethoxy)aluminum hydride or catalytic hydrogenation on platinum oxide in HCl aqueous solution.

12. A process as claimed in claim 11, wherein the reducing agent is sodium bis(methoxyethoxy)aluminum hydride, in amounts ranging from 3 to 4 mol per mol of compound (III), at a reaction temperature above 35° C.

13. A process as claimed in claim 9, wherein compound of formula (I) is isolated as free base or salified as hydrochloride or phosphate.

14. A process as claimed in claim 13, wherein the compound of formula (I) is isolated at the end of the process by using a cationic ion exchange resin.

15. A process as claimed in claim 1 wherein is used a compound of formula (VI) is (VI A)

wherein $R_1$ is a $C_1$–$C_4$ alkoxy group.

16. A process as claimed in claim 15, wherein in compound of formula (VI A), $R_1$ is methoxy or ethoxy.

17. A process as claimed in claim 16, wherein compound (VI A) in amounts of at least 1 mol per mol of compound (IV), in absolute ethanol as reaction solvent and at a temperature of 60–70° C.

18. A process as claimed in claim 1, wherein is used a compound (VI), in which $R_1$ is a $C_1$–$C_4$ alkoxy group and A is a —$CHRR_2$ group wherein R and $R_2$ have the meanings defined above.

19. A process as claimed in claim 18, wherein in the compound of formula (VI), $R_1$ is methoxy or ethoxy, and A is a group of formula —$CHRR_2$ in which R is H and $R_2$ is Cl or Br.

20. A process as claimed in claim 19, wherein in step a) ethyl chloroacetate the compound of formula (VI), and is used in amounts of at least 1 mol per mol of compound (IV), in absolute ethanol, at a temperature ranging from 20 to 70° C., in the presence of 1 mol of $Na_2CO_3$ per mol of compound (IV) and for a reaction time ranging from 3 to 36 hours.

21. Compounds of general formula (III), (III)

wherein one of $Y_1$ or $Y_2$ is —$CH_2$—$CH_2$— and the other is a group of formula COCHR wherein R is H or straight or branched $C_1$–$C_4$ alkyl, optionally substituted with one more —OPg groups in which Pg is as defined above, $Y_1$ is CO—CO and $Y_2$ is $CH_2$—$CH_2$.

22. Compounds as claimed in claim 21 wherein R is H, straight or branched $C_1$–$C_4$ alkyl, optionally substituted with one or more benzyl-protected hydroxy groups.

23. A compound as claimed in claim 21, of formulae (XII) and (XIII)

(XII)
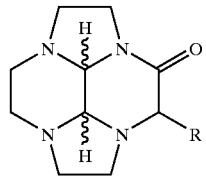

(XIII)
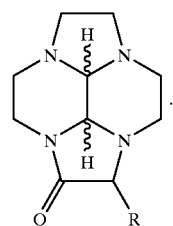

24. A compound as claimed in claim 23, of formulae (XII A), (XIII A) and (XIII B)

(XII A)
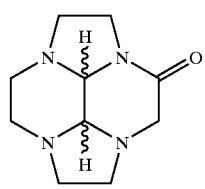

(XIII A)
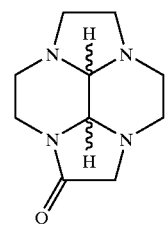

(XIII B)
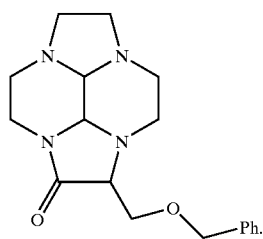

25. Compounds of formula (I)

(I)
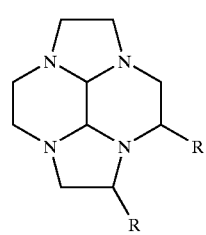

wherein one of the groups R is hydrogen and the other is straight or branched $C_1$–$C_4$ alkyl, optionally substituted with one or more groups —OPg in which Pg is a hydroxy-protecting group.

26. The compound of formula (I B)

(I B)
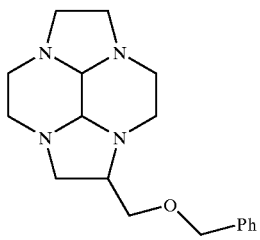

which is 2-phenylmethoxymethyl-decahydro-2a,4a,6a,8a-tetraazacyclo-pent[fg]acenaphthylene.

27. The compound of formula (XI)

(XI)
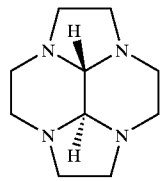

which is trans-decahydro-2a,4a,6a,8a-tetraazacyclopent[fg] acenaphthylene.

28. A compound as claimed in claim 21, of formula (VII) or (VIII)

(VII)
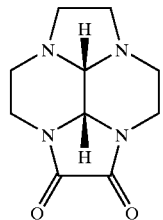

(VIII)
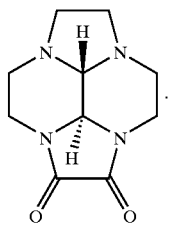

29. A compound of the formula (X)

(X)
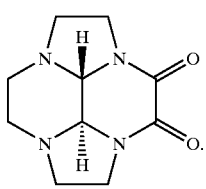

* * * * *